United States Patent [19]

Ward

[11] 4,192,727

[45] Mar. 11, 1980

[54] POLYELECTROLYTE HYDROGELS AND METHODS OF THEIR PREPARATION

[75] Inventor: James A. Ward, Goshen, N.Y.

[73] Assignee: Union Carbide Corporation, New York, N.Y.

[21] Appl. No.: 821,082

[22] Filed: Aug. 3, 1977

Related U.S. Application Data

[63] Continuation-in-part of Ser. No. 717,397, Aug. 24, 1976, abandoned.

[51] Int. Cl.$^2$ .................................................. C08F 2/54
[52] U.S. Cl. .............................. 204/159.12; 128/156; 128/284; 128/287; 128/290 R; 204/159.13; 204/159.16; 204/159.22; 521/137; 260/17 A; 260/17.4 R; 260/17.4 CL; 260/17.4 ST; 260/29.6 RW; 260/29.6 WB; 260/29.6 H

[58] Field of Search ............... 204/159.22, 159.23, 204/159.24, 159.12, 159.13, 159.16; 260/29.6 H, 29.6 RW, 29.6 WB

[56] References Cited

U.S. PATENT DOCUMENTS

| | | | |
|---|---|---|---|
| 3,810,468 | 5/1974 | Harper et al. | 128/156 |
| 3,901,236 | 8/1975 | Assarsson et al. | 128/284 |
| 3,926,756 | 12/1975 | Restaino | 204/159.22 |
| 3,948,740 | 4/1976 | Phalangas | 204/159.23 |

*Primary Examiner*—Walter C. Danison
*Attorney, Agent, or Firm*—William Raymond Moran

[57] ABSTRACT

A predetermined mass comprising an acrylate salt and acrylamide is exposed to a controlled intensity and dose of ionizing radiation effecting simultaneous cross-linking and polymerization thereof to form a polyelectrolyte hydrogel. The resulting hydrogel is an insoluble hydrophilic copolymer which can contain or when dried absorb large quantities of aqueous fluids.

54 Claims, No Drawings

POLYELECTROLYTE HYDROGELS AND METHODS OF THEIR PREPARATION

RELATED APPLICATION

This application is a continuation-in-part of U.S. patent application Ser. No. 717,397 filed Aug. 24, 1976, now abandoned, by J. A. Ward.

This invention relates to polyelectrolyte polymers which are water insoluble but water swellable and methods for producing them. More particularly, this invention relates to cross-linked, random copolymers comprised of an acrylate salt and acrylamide and methods of producing them by means of a controlled dose and controlled intensity of ionizing radiation.

It is well known in the prior art that acrylic acid and its salts may be polymerized under the influence of high energy ionizing radiation. For example, U.S. Pat. No. 3,090,736 relates to a method of employing high energy ionizing radiation to polymerize and cross-link water-soluble salts of acrylic acid to form water insoluble polymers. And U.S. Pat. No. 3,764,502 discloses a process for irradiating acrylate monomers at very low dose rates to produce water soluble polymers.

This invention is based upon the discovery that hydrophilic copolymers which are water insoluble and possess superior absorption properties can be prepared in a single step by subjecting a predetermined mass comprising an aqueous solution of a mixture of monomers to a controlled dose and controlled intensity of ionizing radiation. This mixture of monomers comprises acrylamide and at least one acrylate salt. Alternative methods of preparing these hydrophilic copolymers have been discovered wherein the predetermined mass also includes a thickening agent, absorbent material or filler material or combinations thereof.

Accordingly, it is an object of this invention to provide a hydrophilic, insoluble copolymer having a superior combination of properties and methods for its production. Another object is to provide a hydrophilic, insoluble copolymer and method for its production by means of irradiation of an aqueous solution of acrylamide and at least one acrylate salt to simultaneously cross-link and polymerize the solution. An object is to provide a hydrophilic, insoluble copolymer and method for its production by means of irradiation of a predetermined mass to simultaneously cross-link and polymerize it, the predetermined mass comprising an aqueous solution of acrylamide and at least one acrylate salt which solution has been contacted with a thickening agent, absorbent material or filler material or any combination thereof. Still another object is to provide methods for producing an acrylamide-acrylic acid copolymer having superior absorptive properties compared to an acrylic acid polymer obtained in the absence of acrylamide, and the copolymer produced thereby. Another object is to provide methods for producing water insoluble hydrogels at a controlled dose and intensity of ionizing radiation. An object of this invention is to provide a method for producing hydrogels from thickened solutions which are firmer and as absorptive as hydrogels produced from aqueous solutions containing only the monomers, at equivalent doses. Another object is to provide methods for insolubilizing and cross-linking a predetermined mass comprised of an acrylate salt and acrylamide without the use of chemical cross-linking agents. An object of this invention is to provide methods for producing polyelectrolyte hydrogels from aqueous solutions having high concentrations of an acrylate salt and acrylamide mixture. These and other objects will readily become apparent to those skilled in the art in the light of the teachings herein set forth.

In its broadest aspect, this invention is directed to a method for cross-linking and polymerizing a predetermined mass comprised of a mixture of at least one acrylic salt and acrylamide and to the products obtained therefrom. The method of this invention comprises simultaneously cross-linking and polymerizing, by irradiation, a predetermined mass comprising a mixture of acrylamide and at least one acrylic salt.

Any acrylate salt is suitable for the method of this invention. Suitable acrylate salts include acrylates of an alkali metal, ammonium, calcium, magnesium, tin, lead, strontium, nickel, zinc, barium, cobalt, cadmium and mixtures thereof. Preferred acrylate salts include sodium acrylate, potassium acrylate and ammonium acrylate.

The method of forming an insoluble polyelectrolyte polymer of this invention comprises:

(a) forming a predetermined mass comprised of a mixture of an acrylate salt and acrylamide in a ratio of acrylate salt to acrylamide between about 0.15 to 1 and 20 to 1, the predetermined mass having a pH in solution between about 6 and 12; and (b) exposing the predetermined mass to a dose rate up to about 10 megarads per second or at a dose rate varying in intensity between a first level and a second level for a time period sufficient to form a water insoluble hydrogel which is substantially free of unreacted monomer.

By the term "polyelectrolyte", as employed in the specification, is meant a polymer with ionic groups in the chain or as pendant groups; the ionic groups are negative and are called polyanions. By the term "hydrogel" as employed in the specification is meant an insoluble organic compound which has absorbed aqueous fluids and is capable of retaining them under moderate pressures. By the term "dose rate" as employed in the specification is meant the amount of energy absorbed per unit weight per unit time.

The insoluble polyelectrolyte polymers of this invention are defined as hydrogels when they are in the state of having absorbed an aqueous media. The polyelectrolyte polymers can repeatedly and reversibly absorb and desorb aqueous media. Hence, it can be said that the polyelectrolyte polymers of this invention can oscillate between water-loaded and dewatered states, the polymer defined as a hydrogel in its water-loaded state. Hydrogels of this invention will reversibly desorb water to other hydrophilic materials in contact therewith or evaporate water to the atmosphere.

The term "insoluble" or "insolubilize" as employed throughout the specification is used herein to refer to the formation of a material, at least about sixty percent (60%), preferably at least about eighty percent (80%) of which is essentially insoluble in aqueous media.

The polyelectrolyte polymer of this invention comprises a cross-linked random copolymer comprised of an acrylate salt and acrylamide wherein the cross-link is a direct covalent bond joining carbon atoms of separate polymer chains and there are no chemical groups such as cross-linking agents between such separate polymer chains. The copolymer comprises acrylate units having the formula:

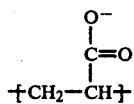

and acrylamide units having the formula:

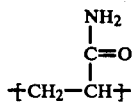

The acrylate units and acrylamide units are present in the copolymer in a random fashion. The ratio of acrylate units to acrylamide units in the copolymer should be up to about 20 to 1. Preferred ratios depend upon the end application of the hydrogels. Where firmer gels are desired, ratios of acrylate units to acrylamide units should be between about 0.15 and about 1/1, preferably between about 0.3 and about 1/1, and most preferably between about 0.4 and about 0.6/1. Where higher capacities for fluids are desired, ratios of acrylate units to acrylamide units can be as low as about 1/1 and as high as about 20/1. Preferably, they are as low as about 5/1 and as high as about 11/1, and most preferably are about 10/1.

The cross-linked random copolymer comprised of an acrylate salt and acrylamide of this invention differs structurally from a copolymer of acrylate salt and acrylamide produced by chemical cross-linking. For example, the cross-links of the copolymer of this invention can be illustrated by the following unit:

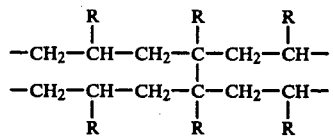

wherein R represents an amide or carboxyl group. And a chemically cross-linked copolymer of acrylic acid or its alkali metal salt and acrylamide such as described in U.S. Pat. No. 3,686,024 can be illustrated by the following unit:

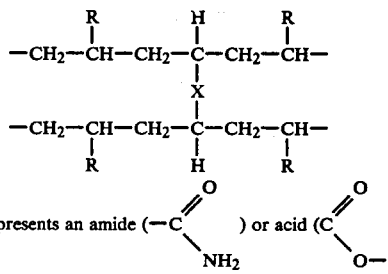

group and X represents a portion of a chemical cross-linking monomer such as methylenebisacrylamide.

The X group in the chemically cross-linked copolymer of acrylic acid and acrylamide is hydrolyzable and therefore unstable in many applications, particularly in the presence of basic solutions. On the other hand, the copolymer of this invention, cross-linked by ionizing radiation, is characterized by the absence of hydrolyzable or otherwise potentially labile groups either in the polymer chain or as part of the cross-link.

The number of cross-links in the copolymer of this invention can vary over a wide range from one or two per polymer chain up to fifty or more. There can be as few as one cross-linked group (acrylate or acrylamide) per every 10,000 groups. And there can be as many as one cross-linked group per ten groups. Fewer cross-linked groups result in a copolymer having a high capacity for fluids but somewhat weaker in gel strength, i.e. not as firm. A greater number of cross-linked groups would provide copolymers having larger gel strengths but lower capacities for fluids. The copolymer produced according to the method of this invention should have acrylate units and acrylamide units randomly linked therein with the total molecular weight of acrylate and/or acrylamide units between cross-links in the range of from about 500 to about 4,000,000 and preferably from about 1000 to about 500,000.

The cross-linked and polymerized products of this invention, as previously indicated, are insoluble hydrogels which have a homogeneous appearance and properties which include low residual monomer levels and absence of unstable or hydrolyzable groups in the polymer network. The ratio of carboxyl groups to amide group can vary greatly in the hydrogel, e.g., the percent of carboxyl (acrylic acid) groups in the hydrogel can vary from 13% to 95% by weight.

Moreover, the polyelectrolyte hydrogels of this invention have many desirable properties and many potential advantages over non-ionic absorbents such as poly (ethylene oxide) containing hydrogels. Because of their (poly) ionic character, polyelectrolyte hydrogels are capable of absorbing very large quantities of aqueous solutions. Normally, the absorption rate is also faster than their non-ionic counterparts. The polyelectrolyte gels of this invention are capable of absorbing up to about 1,000 times their own weight of deionized water. However, this absorption is altered by the presence of salts, i.e., the presence of other ionic constituents in the aqueous solution. For example, the polyelectrolyte hydrogels will absorb several hundred times their weight in tap water and about fifty times their weight in 0.3 N saline solution. By contrast, typical non-ionic poly (ethylene oxide) hydrogels are capable of absorbing in the order of fifty times their own weight regardless whether the fluid is deionized water, tap water or saline solution.

As previously mentioned, depending on the end applications, polyelectrolyte polymers of the invention may be produced having a preponderance of either carboxyl groups or acrylamide groups. When it is desirable to obtain firmer hydrogels and the water capacity is not of prime concern such as in battery separator applications, polyelectrolyte polymers having a preponderance of acrylamide groups should be employed. And when it is desirable to obtain hydrogels having a large capacity for fluids and where the presence of residual acrylamide groups is undesirable, such as in disposable absorbent article application, polyelectrolyte polymers having a preponderance of carboxyl groups should be employed.

Accordingly, in one embodiment of this invention, a concentrated aqueous solution of an acrylate salt containing a majority of carboxyl groups is prepared. Acrylic acid is contacted with a base and water to form an acrylate salt solution. Suitable bases which may be employed to neutralize acrylic acid in forming the corresponding acrylate salt include alkali metal hydroxides, ammonium hydroxide, potassium carbonate and the like. The solution so formed contains a concentration of acrylate salt between about 20 and about 40 weight percent, preferably about 30 weight percent.

Acrylamide is contacted with the acrylate salt solution to form a solution containing a mixture of an acrylate salt and acrylamide. In this embodiment, the acrylamide in the mixture should be present in a concentration of up to 25 weight percent based upon the weight of the total solution, preferably being present in a concentration between about 1 percent and about 10 percent.

The monomer units of acrylamide and acrylate salt present in the solution should be greater than about 20 percent by weight based upon the weight of the total solution, and preferably are present in the solution in a concentration greater than about 30 weight percent. High concentrations of monomer units by weight such as those employed in the method of this invention are desirable. High monomer concentrations require a smaller irradiation dose to produce hydrogels and hence are more economical.

In another embodiment of this invention, solutions containing the monomer units of an acrylate salt and acrylamide are formed as described previously. However, amounts of each monomer units are varied so as to provide a preponderance of acrylamide groups. The solution containing the monomer units should comprise less than about 20 percent by weight of acrylate salt units and between about 20 and 50 percent by weight acrylamide groups.

The polyelectrolyte hydrogels of this invention may be prepared over a wide range of pH. In order to maximize their potential absorptive capacity, their pH should be between about 5 and about 12, i.e., in the range wherein virtually all of the acrylic acid has been neutralized. In solutions neutralized with ammonia, i.e., in ammonium acrylates solutions, it has been observed that their pH should be in the range of from about 5 to 8. The hydrogels of this invention may also be produced at pH's in the range of from about 2 to 5, but these conditions would require an additional neutralization step to maximize the absorptive capacity of the hydrogel.

Water-insoluble, hydrophilic, cross-linked copolymers are produced by subjecting the previously described solutions of monomer mixtures, to sufficient ionizing radiation to simultaneously polymerize and cross-link the solutions of monomer mixtures. As used herein, the term "ionizing radiation" includes that radiation which has sufficient energy to cause electronic excitation and/or ionization in the polymer molecules or solvent molecules (where a solvent is employed) but which does not have sufficient energy to affect the nuclei of the constituent atoms. The high energy ionizing radiation employed may be electromagnetic or particulate in nature, and includes accelerated electrons, protons, neutrons, etc., as well as X-rays and gamma rays. Convenient sources of suitable ionizing radiation are gamma ray-producing radio-isotopes such as $Co^{60}$ and $Cs^{137}$, spent nuclear fuel elements, X-rays such as those produced by conventional X-ray machines, and electrons produced by such means as Van de Graaff accelerators, linear electron accelerators, resonance transformers, and the like. Suitable ionizing radiation for use in the present invention will generally have an energy level in the range of from about 0.05 MeV to about 20 MeV.

The irradiation of the monomer units can be carried out in the solid phase or in solution. Solid monomer mixtures can be irradiated in the air, in a vacuum, or under various gaseous atmospheres, while irradiation in solution can be carried out with the monomers dissolved in water, in organic solvents of high dielectric constant, or in mixtures of water and water-miscible organic solvents. Any conventional method can be used to bring the solid monomer mixtures or monomer mixtures in solution into contact with the ionizing radiation. Suitable methods are well known and understood by those skilled in the art.

When a non-viscous, aqueous solution of monomer mixtures is conveyed through an irradiation field, it is important to maintain the desired dimensions of the aqueous solution so that each portion thereof is irradiated in a homogeneous fashion as discussed more fully subsequently herein. One possible method of accomplishing this control is filling the containers with the aqueous solution, the containers having the desired shape and dimensions, conveying the filled containers through the irradiation field, and removing the insoluble polyelectrolyte polymer products from the containers.

Alternative methods of forming an insoluble polyelectrolyte polymer in a continuous manner have been discovered which immobilize the aqueous solution and transform it into a form whose dimensions can be easily defined and controlled without the use of containers. These methods employ a processing additive which aids in conveying the aqueous solution into the irradiation field and allows the use of conventional casting techniques in handling the aqueous solution. According to these methods, a processing additive comprising a thickening agent, absorbent material, or filler material or combinations thereof is admixed with the predetermined mass comprised of the aqueous solution prior to the irradiation step to immobilize the predetermined mass and substantially restrict it from flowing.

Conventional casting techniques involve casting the material onto a support medium as described more fully in *Coating Equipment and Processes,* George L. Booth, (Lockwood Publishing Co., Inc., New York, New York at pp. 197–209 1970), incorporated herein by reference. Casting (coating) non-viscous aqueous solutions onto a support medium is difficult since they tend to flow off the backing, making control of the thickness (depth) of the solution a problem. Incorporating a thickening agent into the monomer mixture solution provides a means of controlling the dimensions of the thickened product solution. Controlling the viscosity of the thickened solution assures that its flow rate will be sufficiently slow that only slight movements will be noticed during the short time span between the initial casting step and the irradiation step. Generally, this time span is on the order of minutes.

It should be appreciated that longer time periods between the casting and irradiation steps may require use of solution with higher viscosities than are required for shorter time periods. It should also be appreciated that once the solution begins to be irradiated, the polymerization reactions initiated by the irradiation will quickly thicken and solidify the solution. A very viscous hydrogel will form and the control afforded by the thickener is no longer needed.

The required viscosity of the solution then is a function of the casting technique employed. Different casting systems, e.g., casting onto a horizontal moving belt, or onto a vertical or inclined conveying belt could be used. These different casting systems would, in turn, require different viscosity specifications for the solutions to be cast.

In addition to processing advantages obtained by using properly thickened solutions, it has been found that the use of thickening agents provides other benefits. In brief, these benefits are that less dose is required to produce equivalent hydrogels, i.e., the thickening agent tends to cause the thickened target solution to more effectively utilize the radiation to which it is exposed. Consequently, a firmer hydrogel having the desired high absorption capacity can be produced at a smaller dose than required by the non-thickened solution. The overall result is that the throughout, the amount of hydrogel produced per unit time, is greater and therefore, the expense of the irradiation step is smaller.

It is believed that the explanation for this unexpected result is as follows: The process can be visualized as occurring in two steps—an initial polymerization step providing high molecular weight (linear) polymer molecules followed by cross-linking reactions which join these molecules together into a hydrogel network. The presence of some high molecular weight polymers at the beginning can be visualized as providing grafting sites on which the polymerization can occur efficiently. However, the real benefit is more likely due to more efficient cross-linking. Additionally, the so-called Trommsdorf effect or gel effect predicts that in highly viscous solutions or gels, termination reactions are considerably less favored, leading to longer polymerization chain lengths and, hence, higher molecular weight polymers. The decrease in required dose when solutions were thickened with hydroxyethylcellulose was, for example, quite unexpected. It is believed that this is due to an increased grafting efficiency on the cellulose backbone.

In one alternative embodiment of the method of this invention, a thickened solution is cast, by well-known techniques, onto a backing of paper, an open mesh scrim, a steel belt, or the like. The casting is performed continuously, and, the thickened target solution is conveyed in a continuous manner through the irradiation field. In the absence of a thickening agent, the non-viscous, aqueous target solution would flow and tend to run off the backing. Moreover, in the absence of a thickening agent, it would also be difficult to control the flow of a non-viscous, aqueous target solution from a casting apparatus.

With a thickening agent present, control of the thickened target solution is easily maintained. Viscous solutions do not flow readily. Therefore, both the thickness (depth) and width of the cast thickened solution will be substantially constant for the short time periods necessary for the cast thickened solution to travel from the casting (coating) head to the irradiation field.

Use of viscous target solutions not only provides a means of process control, but also provides other options. It may be desirable to irradiate a target solution while it is being conveyed on an inclined plane or even vertically past the source of ionizing radiation. A thickened target solution permits such flexibility. Or the conveying system itself may be non-planar, e.g. curved or concave as discussed subsequently herein. Again, a thickened target solution would not, once cast onto such a curved or concave shaped conveyor belt, flow off of the conveyor belt. Moreover, the cast target solution assumes the contoured shape of the conveyer belt, allowing irradiation of target solutions in a wide variety of shapes. Other shapes and configurations for the conveying system are possible and are easily handled with a thickened target solution.

Homogeneity of the dose delivered to the target solution is desired. It is recognized that no radiation process, particularly no accelerated electron process, provides a truly uniform dose distribution. Typically, the dose delivered to a target solution increases with the distance away from the source of radiation to a maximum and then decreases. As a result, the dose received at the surface of a target solution (closest to the source of radiation) is generally smaller than that received within the solution. If a thin enough (depth) target solution is employed, the dose distribution received is substantially uniform. When thicker solutions are employed, the dose received per unit cross-sectional area as a function of distance away from the irradiation source gradually increases to a maximum and then gradually decreases.

The equal entrace-exit point is the depth of the target solution where the bottom cross-section (exit) furthest away from the irradiation source receives the same dose as the top cross-section (entrance). With a 1.5 MeV Van de Graff accelerator, an equal entrance-exit point of about 4.5 mm was measured. When target solutions whose thickness is less than or equal to the equal entrance-exit depth (for the irradiation source employed) are employed, the maximum variation in dose is less than a factor of two.

Another variation in dose homogeneity is a function of the distance between the target solution and the irradiation source. For example, when an electron accelerator is used, a fast electron therefrom can interact with an air molecule. This interaction usually involves a release of (a small portion of its) energy and a slight change in direction. Increasing the distance between the accelerator and the target solution allows for more interactions and deflections. The magnitude of this effect is surprisingly large. It has been found that passing electrons through two feet of air is equivalent to passing them through approximately 1 mm of unit density material. Moreover by the time the electrons traveled a distance of two feet in the vertical direction, they spread out from an initial width of 0.5 inches (at the source) to a width in excess of 4 feet in the horizontal direction (at the target solution).

Employing target solutions of narrower width will provide a means of assuring delivery of a homogeneous dose over the entire cross-sectional area of the target solution. However, when distances between the irradiation source and the target solution are increased and/or when the width (cross-sectional area) of the target solution increases, variations in the dose received occur. Assuming the target solution is aligned to pass directly under the irradiation source on a conveyer belt, the central portion of the target solution would receive the maximum dose and the edges of the target solution would receive a smaller dose.

In order to assure a homogeneous dose to the entire cross-sectional area of the target solution facing the irradiation source, the conveyed target solution should be shaped so that its edges are closer to the irradiation source where they would receive a higher dose. For example, the target solution may be concave or V- shaped. Use of a thickened target solution permits its shaping to such a contour. The thickened solution may be cast onto a curved, dish-shaped or concave or V-shaped casting surface (backing material). Since the thickened solution would replicate the shape of the casting surface, delivery of a homogeneous dose thereto would be possible. Wide target solutions can be irradiated according to the method of this invention with efficient utilization of the output energy of the irradiation source resulting in significant increases in throughput.

It has been found that high molecular weight thickening agents such as poly (acrylamide), poly (ethylene oxide) and hydrooxyethylcellulose provide excellent viscosity building characteristics for the acqueous solutions made according to the methods of this invention. Lower molecular weight versions of these three thickening agents may also be employed, but in higher concentrations to achieve comparable viscosities for the thickened solution. Moreover, Gelgard particles, XD-1300 (Gelgard is a trademark for a cross-linked, partially hydrolyzed polyacrylamide, 40% hydrolyzed and sized finer than 100 mesh, made by Dow Chemical Company) and ground up "fine particles" of the polyelectrolyte polymer made according to the methods of this invention (finer than 60 mesh) also provide excellent viscosity building characteristics for the aqueous solutions made according to the methods of this invention.

In general, high molecular weight versions of water soluble polymers that are capable of increasing the viscosity of an aqueous solution to above about 5,000 centipoise would be suitable as thickening agents for the methods of this invention. Illustrative of water soluble polymers which are believed to be suitable thickening agents are the following: sodium carboxy methyl cellulose (cellulose gum); partially hydrolyzed poly (acrylamide); polyacrylic acid; poly (vinyl alcohol); natural occurring water soluble polymers such as Guar gum and starch; poly (vinyl pyrrollidone); Xanthan gum; poly (ethylene imine); polyethylene sulfonate, polystyrene sulfonate; hydroxypropyl cellulose; and methyl cellulose.

The thickening agent is admixed with the aqueous solution of monomer mixtures in an amount up to about 50%, preferably up to about 10%, and most preferably between about 0.5% and about 6%, by weight of the product hydrogel. The thickening agent is added in an amount sufficient to increase the viscosity of the aqueous solution of monomer mixtures to the range of about five thousand centipoise to about one million centipoise, preferably between a range of about ten thousand centipoise to about fifty thousand centipoise. Handling of the thickened solutions at viscosities above about one million becomes difficult and hence viscosities above one million are unnecessary. The lower limit of viscosity needed is a function of the distance between the casting head and the source of ionizing radiation as well as the conveyor speed.

The thickening agent dissolves in and thickens the monomer mixture solution. Since water is a major constituent of the solution, water soluble polymers are preferred. However, due to the fact that, in certain formulations, the monomers constitute about 50 percent of the solution, non-water-soluble polymers may also be effective.

The thickening agent is added to and dispersed within the aqueous solution of monomer mixtures, prepared as described previously herein, in a slow, controlled fashion preferably in the form of a powder. A vibrating tray situated above the aqueous solution may be employed to disperse the powdered thickening agent into the aqueous solution. The powder is shaken from the tray in a controlled manner so that only small amounts of the particles contact the surface of the solution at any one time. Simultaneously, the aqueous solution is mixed, effectively dispersing the powder. After the initial dispersion, the solution is mixed for a period of time sufficient to dissolve the powdered particles therein. The viscosity of the thickened solution increases and approaches its equilibrium value after several hours, depending upon the amount of powder added and the ultimate viscosity to be achieved. The viscosity of the thickened solution should be sufficiently high, however, to allow control of the dimensions of the thickened solution upon its casting. In addition, the viscosity of the thickened solution should be sufficiently low, to permit transport of the thickened solution from the mixing zone to a casting (coating) head via a pump and appropriate (stainless steel) tubing or the like.

The order in which individual components of the thickened solution are added in its formation is essentially immaterial. It may be desirable to thicken one or more of the individual components before they are mixed. Or a simultaneous mixing, neutralization, and thickening procedure could be worked out. Or an initial dispersion of the thickening agent into one of the individual components, followed by a final simultaneous mixing and thickening step could be employed.

Methods alternative to increasing the viscosity of the acqueous solution may also be employed to provide dimensional control of the solution to be cast. For example, the aqueous solution may be contacted with or deposited on or into an absorbent material to form a composite. The composite comprises a matrix of absorbent material which has entrapped therein an aqueous solution of monomer mixtures. This composite may be easily handled and conveyed through the irradiation field.

Still another processing additive which provides a method of preparing the polyelectrolyte polymers of this invention other than substantially increasing the viscosity of the aqueous solution involves the use of a filler material. A filler material may be admixed with the aqueous solution to aid in conveying the mixture thus formed through the irradiation field. The filler material absorbs or immobilizes the aqueous solution. The mixture of filler material and aqueous solution can be put in motion but will not flow by itself. The mixture has the flow properties of the filler material contained therein.

Suitable filler and absorbent materials include cellulose such as cotton fibers and modified cellulose; silica; clay based materials such as bentonite; wood flour; paper; perlite; vermiculite and hydrophilic polyurethane foam.

Filler materials and absorbent materials are materials which when added to an aqueous solution immobilize it. The flow characteristics of mixture or composite which is formed are more similar to the filler or absorbent material contained therein than the aqueous solution contained therein. Filler materials are capable of surface absorption and absorbent materials entrap the aqueous solution within their porous structure.

The amount of filler material added to the aqueous solution should be between about 10% and about 90% by weight of the product mixture, preferably between about 25% and about 75% by weight of the product mixture (of aqueous solution and filler material). The amount of absorbent material should be less than about 50%, preferably less than about 10% by weight of the product composite (of absorbent material and aqueous solution).

The random copolymerization of the predetermined mass containing the monomer unit mixtures results from the action of ionizing radiation. A radical is formed as a consequence of the absorption of part of the energy of incident particles. This radical initiates the polymerization in that it forms, by one of several possible reactions, a radical site on a monomer. This monomer radical then is more reactive toward other monomer molecules. It is known that the reactivities of acrylamide and acrylate anion are not grossly different. Thus, it is approximately equally likely that the monomer radical will subsequently react with either of the two monomers present. There should be no portions of the polymer chain containing exclusively one type of group. That is, a polymer formed with many acrylamide groups all joined together with no intervening acrylate salt groups is quite unlikely. In short, the resulting polymer will be a random copolymer with the acrylamide and acrylate salt groups randomly distributed along the chain.

The cross-linking of the polymer also results from the action of ionizing radiation. A radical formed either from the direct action of radiation or possibly a growing polymer chain, abstracts in some way a hydrogen atom from one of the carbon atoms on a polymer chain. This polymer chain, now minus a hydrogen, is a radical which can then react. The cross-linking reaction occurs when two such polymer radicals combine.

The position of the cross-link is, in most cases, determined by the ease of the abstraction reaction. Thus, it is more likely that the abstraction will occur at the carbon atom having the weakest carbon hydrogen bond. For acrylamide and acrylate salt copolymers, this weak carbon-hydrogen bond is situated where the acrylamide or acrylate salt group is also attached. It is believed that the presence of acrylamide results in better cross-linking than possible when a solution containing only acrylate groups is exposed to ionizing radiation. Cross-linking of a solution of acrylate groups alone is inhibited or slowed down due to ionic repulsion of like charges of acrylate groups. The like charges tend to keep the molecules apart. On the other hand, when acrylamide is present in addition to the acrylate groups in solution, the presence of the non-ionic acrylamide groups reduces the tendency of acrylate salts to repulse each other.

The exact amount of ionizing radiation to which the predetermined mass must be subjected depends on a number of variables. While it is possible to produce hydrogels at very high dose rates, the does, i.e., the total amount of energy absorbed by the target predetermined mass comprising an aqueous solution, needs to be rather large. A reduction in dose rate leads to a substantial drop in the dose required to produce suitable hydrogels. Further decreasing the dose rate results in a still further decrease in the required dose. However, there exists a dose rate level below which irradiation becomes impractical and uneconomical.

This invention is based on the discovery that insoluble, hydrophilic copolymers in the form of hydrogels can be conveniently prepared at controlled intensities and doses of irradiation. Hence, according to the method of this invention, the hydrogels are prepared by irradiating an aqueous solution of certain monomer mixtures while employing ionizing radiation having an energy level in the range of about 0.10 MeV to about 20 MeV at a fixed or varying dose rate for a total dose up to about 10 Megarads, but preferably more than about 0.2 Megarads and less than about 3 Megarads.

The dose rate may be uniformly applied to the aqueous solution of monomer mixtures or may be varied between a first level and a second level. Preferably, the first level is greater than about 0.0001 Megarads per second and less than the second level. And it is also preferred that the second level be greater than the first level and less than about 0.5 Megarads per second.

One means of providing a fixed dose rate is to cause a source of ionizing radiation to be very close to the solution to be irradiated. The source delivers the desired dose directly into and through the solution. If desired, the solution may be passed by the source of ionizing radiation at close range or the source of ionizing radiation may be passed by the solution at a velocity sufficient to deliver the desired dose at a fixed dose rate.

A varying dose may be conveniently obtained by causing the source of ionizing radiation to be in the vicinity of, but not extremely close to the solution to be irradiated. The solution may be passed by the source of ionizing radiation at a preselected distance as subsequently discussed, or the source of ionizing radiation may be passed by the solution at a velocity sufficient to deliver the desired dose at a varying dose rate. The source emits beams of radiation which spread out and strike a larger target area as the distance between the source and the solution to be irradiated increases. Also, as this distance increases the intensity of the beams of radiation decreases. Selection of the distance between the source and the target solution and the energy level of the source determines then the variations in dose rate delivered to the target solution and their intensities. The target solution should be exposed to the beams of radiation for a period of time sufficient to receive delivery of the desired dose. This time period is generally longer than that required to deliver an equivalent dose at a fixed dose rate.

The dose of ionizing radiation delivered to the predetermined which comprises an aqueous solution of monomer mixtures fully penetrates the solution and may pass therethrough. Moreover, the dose of ionizing radiation overcomes the free radical scavenger inhibitors present in the monomers to cross-link and polymerize the aqueous solution. It may be desirable, at times to remove the free radical scavengers prior to irradiation, but this is not necessary to this invention.

At doses between about 0.3 to about 10 Megarads and fixed dose rates less than about 0.001 Megarads per second, it has been found that the amount of residual acrylamide increases for hydrogels having comparable water capacity. Moreover, the reaction rate for producing the hydrogel becomes undesirably slow. Furthermore, hydrogels produced at fixed dose rates greater than about 12 Megarads per second at doses between about 0.3 Megarads and about 10 Megarads posses inferior properties such as a low maximum absorptive capacity and high residual monomer levels.

The hydrogel produced according to this invention should have a gel strength of greater than about 0.3 p.s.i., preferably greater than 0.5 p.s.i., Gel strengths are measured in the following manner. A 20 mesh (U.S. Standard Sieve Series) stainless steel screen is attached to cover the mouth of the cylinder. Approximately 100 grams of swollen hydrogel particles, swollen to equilibrium in excess tap water is added to the cylinder. The particle size of the swollen hydrogel must be larger than the pore size of the screen. For example, a polymer particle having a size greater than 80 mesh (U.S. Standard Sieve Series), i.e., it is stopped by an 80 mesh screen, normally will swell to a size larger than 20 mesh. Therefore, the swollen hydrogel will not pass through the screen until pressure was applied.

The pressure needed to extrude the hydrogel through the screen is determined by applying a piston toward the screen and a series of weights to the piston. Pressure is increased until a pressure is reached at which the hydrogel will extrude continuously. From knowledge of the weight applied and the cross-sectional area of the piston, a pressure in pounds per square inch can be calculated at the point at which the hydrogel continuously extrudes through the 20 mesh (U.S. Standard Sieve Series) screen. This pressure is termed gel strength.

In an embodiment of this invention, a dewatered hydrogel may be conveniently prepared by drying the hydrogel produced according to this invention. Drying is accomplished by any conventional method such as heating the hydrogel at a temperature from about ambient temperature to about 200° C. on a drum, in an oven or the like.

The insoluble, hydrophilic cross-linked copolymers which are prepared by the method of this invention are useful in a wide variety of fields. For example, the hydrogels can contain, or when dried, absorb large quantities of aqueous fluids and hence are useful as absorbing media for disposable absorbent articles, such as diapers, or catamenial devices such as sanitary napkins, incontinent pads and tampons, battery separators, fire fighting gels, explosive water gels, gelled insecticides and fungicides and the like.

The insoluble hydrophilic polymers prepared by the methods of this present invention, are particularly useful because they possess the ability to incorporate very large amounts of tap water on the order about 50 to about 500 times their dry weight, preferably greater than about 200 times their dry weight. The insoluble copolymers are able to absorb more than 10 times their dry weight in an aqueous solution of 0.3 N NaCl, and preferably more than 25 times their dry weight. Moreover in addition to possessing the ability to incorporate large amounts of water, they are insoluble in water irrespective of temperature and will retain liquids, solutions and suspensions.

In general, the aforementioned gels are useful for increasing the absorbency of any known or commercially available disposable article. For example, the hydrogels can be incorporated into diapers of the type disclosed in U.S. Pat. Nos. 2,788,003; 2,860,637; 3,306,293 and 2,667,168. Similarly, they can be incorporated into tampons or sanitary napkins of the type disclosed in U.S. Pat. Nos. 3,212,427; 3,070,095 and the like. The gels can be employed in a wide variety of ways, such as, for example, a powder dispersed in and bonded to a cellulosic or similar substrate. Any of the several known methods can be employed to affix the powdered hydrogel to the substrate.

In general, the amount of hydrogel employed will be dependent upon the particular absorbent article and its intended use. In practice, it has been observed that disposable absorbent articles can be prepared containing from about 2 to about 98 weight percent, of the insoluble copolymers, based on the total weight of said article.

EXAMPLE 1

EFFECT OF REDUCED DOSE RATES ON SODIUM ACRYLATE-ACRYLAMIDE GELS

A stock 30 percent by volume acrylic acid solution was prepared from 300 cc glacial acrylic acid, the appropriate amount of concentrated (50 percent) sodium hydroxide to bring the solution to the listed pH and sufficient water to make one liter of solution. The concentrated sodium hydroxide (50 percent by weight) was prepared separately by mixing equal weights of deionized water and sodium hydroxide pellets. The sodium hydroxide solution was then slowly added to the acrylic acid solution with stirring. The temperature was kept below 40° C. Final pH adjustments were done with a more dilute sodium hydroxide solution, if necessary.

The solution can be described as a neutralized 30 percent by volume acrylic acid solution. On a weight basis, the solution can be called 27.2 percent by weight acrylic acid or 35.5 percent by weight sodium acrylate. On a molar basis, the solution can be described as 4.42 moles per liter.

The stock 30 percent acrylic acid solution was neutralized to pH 10.7 as described above. Nine hundred (900) cc of this stock solution was then mixed with 100 grams of acrylamide. The resulting solution is now 27 percent acrylic acid (by volume) and 10 percent acrylamide (weight/volume). Alternatively, this solution can be described as 32.3 percent sodium acrylate and 8.7 percent acrylamide by weight. A portion of this solution was exposed to 1.5 MeV electrons at an electron beam current of 1600 micro amps, a conveyor speed of 30 feet per minute at a distance of 2 inches in the direction of electron flow. These conditions combine to deliver a dose of 1 Megarad/pass at a dose rate of 12 Mrad/sec.

No gel was produced from solutions given 1 to 2 Megarads at these conditions. A solution given 3 Mrads at 12 Mrads/sec did form some gel which had inferior properties. When this was placed in a salt water solution, the swollen gel was rather runny and pituitous, and not firm enough for any applications.

The same sodium acrylate-acrylamide solution was then irradiated by direct exposure to 1.5 MeV electrons from a Van de Graaff accelerator at a number of electron beam currents. For example, 160 micro amperes of electron beam current corresponded to a constant dose rate of 1.2 Mrads/sec. Other dose rates employed included 0.03, 0.12, and 0.3 Mrads/sec. Irradiations were of 150 mm glass petri dishes containing approximately 50 ml of the sodium acrylate-acrylamide solution which was passed under the electron beam on a conveyor belt having a speed of 3 feet per minute. The absorption capacity of hydrogels produced are calculated as follows:

$$\frac{\text{Weight of the Completely Swollen Gel}}{\text{Original Dry Weight of Sample}} = \text{Fluid absorption}$$

Measurements of the gel strengths of test hydrogels were made using the measurement procedure for gel strength discussed previously. The results of the absorption capacity of the hydrogels produced are listed in Table I hereinbelow and the results of the gel strength measurements are tested in Table II hereinbelow:

TABLE I

SALT WATER (0.3N NaCl) CAPACITIES
OF HYDROGELS MADE FROM
32.3% SODIUM ACRYLATE-8.7% ACRYLAMIDE
BY WEIGHT AT pH 10.7

| | Salt Water Capacity Total Dose | | |
|---|---|---|---|
| Dose Rate | 1 Mrad | 2 Mrads | 3 Mrads |
| 12 Mrad/Sec. | 0 | 0 | 36.8 |
| 1.2 Mrad/Sec. | * | 70.0 | 48.5 |
| 0.3 Mrad/Sec. | 83.2 | 40.1 | 32.6 |
| 0.12 Mrad/Sec. | 38.0 | 32.0 | 25.7 |
| 0.03 Mrad/Sec. | 28.7 | 24.5 | 19.8 |

*Weak pituitous gel produced, capacity not measured

TABLE II

GEL STRENGTH OF HYDROGELS MADE FROM
32.3% SODIUM ACRYLATE-8.7% ACRYLAMIDE
BY WEIGHT AT pH 10.7

| | Gel Strength (psi) (measured in tap water) | | |
|---|---|---|---|
| Dose Rate | 1 Mrad | 2 Mrads | 3 Mrads |
| 12 Mrad/Sec. | ** | ** | * |
| 1.2 Mrad/Sec. | ** | 0.3 | 1.1 |
| 0.3 Mrad/Sec. | 0.3 | 1.5 | >2.1 |
| 0.12 Mrad/Sec. | 1.2 | >2.1 | >2.1 |
| 0.03 Mrad/Sec. | >2.1 | >2.1 | >2.1 |

*Weak pituitous gel produced, gel strength not measured.
**Could not be determined.

As indicated in Table I above, absorption capacity decreases as the dose rate is decreased. It can also be appreciated that reduced dose rates will produce acceptable hydrogels at significantly lower doses. However, the acceptability of a hydrogel will depend on its practical application. In general, it is desirable characteristic of hydrogels that they will absorb large quantities of fluid while maintaining rigidity or firmness. As produced according to the process of this invention, hydrogels having capacities in excess of 80 typically are somewhat runny or pituitous. Hydrogels become more firm as their capacity decreases. But the converse is not necessarily true. A low capacity does not always lead to the required firmness. For example, the 3 Mrads, 12 Mrads/sec. sample is completely unsatisfactory although it has a lower capacity.

Hydrogels having gel strengths greater than 0.5 p.s.i. are desirable. At get strengths below 0.5 p.s.i., the hydrogels are soft. As indicated in Table II above, radiation at lower dose rates leads to hydrogels having higher gel strengths. For example, at a dose rate of 0.03 Mrads/sec. a very firm gel is produced at 1 Megarad whereas at 0.3 Megarads per second, and at 1 Megarad, the gel strength is only 0.3 p.s.i.

Firmness and capacity are two properties of hydrogels that are generally mutually exclusive. It has been found according to this invention that gels from sodium acrylateacrylamide may be provided that have an unusually good blend of both strength and capacity when dose rates between 0.001 Mrads/sec. and about 12 Mrads/sec., preferably below about 1.2 Mrads/sec. are used. Higher irradiation dose rates provide unacceptable gels. Only the largest dose (3 Mrads) gives an acceptable gel at 1.2 Mrads/sec.

EXAMPLE 2

Besides large capacities and adequate firmness of the gels, it is desired to have a high conversion of monomer to gel. One measure of the conversion is the amount of unreacted monomer left in the gels. The same gels which were made in Example 1 were analyzed by a method similar to that described in the Encyclopedia of Industrial Chemical Analysis Volume 4, John Wiley and Sons, Inc. (1967), p. 176.

These tests involved measurements of the absorption of acrylamide and/or acrylic acid at 240 nanometers with an ultra-violet spectrophotometer. Gel samples were allowed to swell in excess saline solution, and the amount of absorption in the filtrate was measured. Corrections were then made to account for the dilution.

Table III shows the results for the same gels listed in Table I which are summarized hereinbelow:

TABLE III

RESIDUAL MONOMER IN GELS
MADE FROM IRRADIATED
3.23% SODIUM ACRYLATE-8.7% ACRYLAMIDE
AT pH 10.7 BY WEIGHT

| | Monomer Content in Dry Gels (%) Total Dose | | |
|---|---|---|---|
| Dose Rate | 1 Mrad | 2 Mrads | 3 Mrads |
| 12 Mrad/Sec | 8 | 4.8 | 3.2 |
| 1.2 Mrad/Sec | 2.0 | .36 | .40 |
| .3 Mrad/Sec | .32 | .16 | .24 |
| .12 Mrad/Sec | .16 | .12 | .16 |
| .03 Mrad/Sec | .12 | .16 | .12 |

It can be readily seen that reduced dose rates do yield products which have lower residual monomer, besides also having the desired properties discussed in Example 1.

EXAMPLE 3

IRRADIATION OF ACRYLAMIDE-ACRYLIC ACID MIXTURES

It is known that certain cross-linking agents, e.g., difunctional monomers such as methylene-bis-acrylamide, do lead to enhanced cross-linking in many situations. However, monofunctional additives are not normally thought of as cross-linking enhancers. For these acrylic acid systems, acrylamide leads to a very marked effect.

Stock solutions of varying ratios of acrylamide and sodium acrylate were prepared, irradiated and analyzed by the methods used in Example 1. For example, to portions of the stock solution, varying amounts of acrylamide were added to prepare the solutions listed in Table IV hereinbelow. As an illustration, to 980 mls of the stock acrylic acid solution, 20 grams of acrylamide were added to produce a solution which is 2 percent acrylamide and 29.4 percent acrylic acid. On a weight percent basis, this solution can be described as 34.9% sodium acrylate and 1.7% acrylamide. By suitable addition of acrylamide, and/or water, the other solutions listed in Table IV were similarly prepared.

Table IV gives results for water capacities of gels made from solutions prepared as described above. Some of these examples have been repeated from the previous example. The results are summarized in Table IV hereinbelow:

TABLE IV

EFFECT ON ACRYLAMIDE ON SALT WATER (0.3N NaCl) CAPACITY OF ACRYLIC ACID GELS

| Sodium Acrylate Conc. (% by weight) | Acrylamide Conc. (% by weight) | Capacity Dose | | |
|---|---|---|---|---|
| | | 1 Mrad | 2 Mrads | 3 Mrads |
| 35.5 | 0 | 60.7 | 45.5 | 35.2 |
| 34.9 | 1.7 | 39.2 | 34.4 | 23.4 |
| 32.3 | 8.7 | 38.0 | 32.0 | 25.7 |
| 19.7 | 17.9 | 34.9 | 25.9 | 20.2 |
| 12.8 | 25 | 34.4 | 24.3 | 18.8 |
| 6.5 | 26.4 | 34.8 | 24.3 | 20.7 |

Dose Rate = .12 Mrad/Sec

All the gels in Table IV had adequate firmness. The 30 percent acrylic acid (35% sodium acrylate by weight) (0% acrylamide) gel at one megarad was somewhat soft and the others were considered to be firm.

The effect of acrylamide can be thought of as reducing the dose required to produce a gel of a desired capacity. In particular, small quantities of acrylamide lead to markedly smaller capacities. The gels containing acrylamide are significantly tighter or firmer than gels made, at comparable doses, from sodium acrylate alone.

EXAMPLE 4

EFFECTIVENESS OF GELS AS DIAPER ABSORBENTS

One of the possible uses of these polyelectrolyte hydrogels is as an absorbent in diapers. In many cases, the ultimate equilibrium capacity of a gel is not a good measure of its performance in diapers. Table V shows that the more highly cross-linked gels absorb as much or more saline solution in these tests as do gels having higher capacities. This better performance is thought to be due to the greater strength or firmness of the swollen gel particles.

TABLE V

ABSORPTION OF ACRYLIC GELS* IN SIMULATED DIAPER TESTS

| Dose Rate | Capacity in Diapers | | |
|---|---|---|---|
| | 1 Mrad | 2 Mrads | 3 Mrads |
| 12 Mrad/Sec | N.D. | N.D. | 7.2 |
| 1.2 Mrad/Sec | 9.7 | 16.7 | 19.5 |
| 0.3 Mrad/Sec | 19.4 | 19.2 | 19.9 |
| .12 Mrad/Sec | 20.1 | 23.0 | 23.5 |
| .03 Mrad/Sec | 24.6 | 21.9 | 20.4 |

*32.3% sodium acrylate - 8.7% acrylamide by weight at pH 10.7; the same gels as in Table I.
N.D. - Not Determined.

The capacity of a gel in these simulated diaper tests was determined in the following manner: two 6"×8" absorption pads made from air-laid sulfate wood pulp fibers, weighing about 6 grams, were sandwiched around a wadding laminate containing 0.25 grams of the gel evenly distributed over the laminate area. Fifty (50) cc of saline fluid (0.3 N NaCl) were poured slowly onto the surface of the pads and allowed to equilibrate for 30 minutes. The wet laminate containing the hydrogel was then removed and the laminate, the upper pad, and the lower pad were separately weighed. Corrections were made for absorption due to the portion of the wet laminate containing no gel. The difference is the weight of fluid absorbed by the gel particles. The capacity is the weight of fluid absorbed divided by the weight of fluid absorbed divided by the weight of the gel.

In these examples, it is apparent that there is a large benefit in producing gels at lower dose rates. It should be realized that the capacity in these tests cannot exceed the equilibrium capacity. Hence, as the dose increases the performance in these tests must eventually become worse. The effect of acrylamide is also apparent in Table IV.

TABLE VI

EFFECT OF ACRYLAMIDE ON ABSORPTION OF ACRYLIC ACID GELS IN SIMULATED DIAPER TESTS

| Sodium Acrylate Conc. (% by weight) | Acrylamide Conc. (% by weight) | Capacity in Diapers | | |
|---|---|---|---|---|
| | | 1 Mrad | 2 Mrads | 3 Mrads |
| 35.5 | 0 | 16.4 | 15.5 | 18.6 |
| 34.9 | 1.7 | 21.6 | 18.5 | 19.5 |
| 32.3 | 8.7 | 20.1 | 23.0 | 23.5 |
| 19.7 | 17.9 | 20.4 | 20.8 | 21.9 |
| 12.8 | 25.0 | 18.5 | 19.2 | 17.7 |
| 6.5 | 26.4 | 16.3 | 11.0 | 17.2 |

All solutions irradiated at a Dose Rate—0.12 Mrad/Sec pH—10.7.

EXAMPLE 5

A 37% by weight potassium acrylate aqueous solution was prepared. To prepare this solution, acrylamide was added in varying amounts to prepare 0%, 2%, 5% and 10% acrylamide containing solutions. It is noted that the potassium acrylate concentrations decreased slightly with the addition of the acrylamide due to dilution by the second monomer. The four solutions prepared were then irradiated and the capacity in 0.3 N NaCl solution and the gel strength of the gels produced was measured in a manner previously described. The results are summarized in Table VII below:

TABLE VII

EFFECT OF ACRYLAMIDE ON GELS MADE FROM POTASSIUM ACRYLATE SOLUTIONS*

| Potassium Acrylate | Acrylamide | Capacity in 0.3N NaCl Solutions | Gel (p.s.i.) Strength |
|---|---|---|---|
| 37% | 0 | ** | <0.1 |
| 36.3% | 2 | 70.6 | ~0.1 |
| 35.2% | 5 | 54.7 | 0.4 |
| 33.6% | 10 | 55.5 | 0.7 |

*Solutions were given 2.25 Mrads at a dose rate of 0.65 Mrads sec; 0.375 Mrad/pass; 6 passes
**A weak, pituitous gel was produced, but a capacity measurement could not be accurately made.

As can be seen from Table VII above, the firmness of the swollen gels increases with increasing acrylamide content. The presence of acrylamide results in the production of good gels under conditions where potassium acrylate alone either does not gel at all or, at best, gives highly inferior products.

EXAMPLE 6

Four solutions were prepared using the procedure described in Example 5. However, in this example, the dose rate was not more or less constant as in Example 5, but the dose rate was varied during the course of irradiation. The monomer mixture in solution were irradiated at a very low dose rate first, less than 0.01 Mrads/sec; the dose rate was then increased up to about 0.13 Mrads/sec and then decreased again.

The dose rate was varied by passing the solution to be irradiated at a fairly large distance, two feet, below the exit window of the accelerator. At this distance, some of the electrons are scattered and their direction changed. The result is that some of the electrons will strike the solution even when the solution is a considerable distance away from the window of the accelerator. In the present case with the solution being carried along a conveyor two feet below the window, some of the electrons reach the solution even at a distance of four feet away from the window, i.e., four feet from the point on the conveyor immediately below the window. However, most of the electrons strike the solution (and, therefore, most of the dose is delivered) at distances less than about two feet from this point on the conveyor.

Capacity and gel strength measurements were made on the test hydrogels produced. The results of irradiating these four solutions at a varying dose rate are summarized in Table VIII hereinbelow.

TABLE VIII
EFFECT OF ACRYLAMIDE ON GELS MADE FROM POTASSIUM ACRYLATE SOLUTIONS*

| Gel Strength (P.S.I.) | | | | Capacity in 0.3N NaCl Solutions | |
|---|---|---|---|---|---|
| Conveyor Speed 4 feet/min. Dose - 2 Mrad | Conveyor Speed = 5 feet/min. Dose - 1.6 Mrad | Potassium Acrylate | Acrylamide | Conveyor Speed = 4 feet/min. Dose - 2 Mrad | Conveyor Speed = 5 feet/min. Dose - 1.6 Mrad |
| 0.2 | ** | 37% | 0% | 48.6 | 54.6 |
| 0.2 | 0.2 | 36.3% | 2% | 76.5 | 59.9 |
| 0.6 | 0.3 | 35.2% | 5% | 50.7 | 69.2 |
| 0.8 | 0.7 | 33.6% | 10% | 50.1 | 57.1 |

*Irradiations at varying dose rate; solutions on conveyor two feet below accelerator window; maximum dose rate = 0.13 Mrad/sec.
**Not determined.

EXAMPLE 7

CONTINUOUS PRODUCTION OF HYDROGEL USING POLY (ACRYLAMIDE) THICKENER

A 34 gallon batch of a 19 weight percent potassium acrylate and 35 weight percent aqueous acrylamide solution was prepared as follows: 219 pounds of a 50 weight percent acrylamide solution was contacted with 38.4 pounds of acrylic acid, followed by the controlled addition of 58.2 pounds of a 50 percent by weight potassium hydroxide solution, 9.8 pounds of high molecular weight poly (acrylamide), P-250 (commercially available from American Cyanamid, Wayne, New Jersey 07470) in powder form was added in a controlled fashion to the aqueous solution to ensure that the powder was properly dispersed. The concentration of powdered polymer was 3 percent by weight. The thickened solution was mixed in a 100 gallon stainless steel tank with a mechanical stirrer at 48 RPM for 20 hours and remained unagitated for two additional days. Then its viscosity was measured using a Brookfield Viscometer and found to be 43,000 centipoise.

The thickened solution was then pumped through a 1.5 inch diameter stainless tubing at a pump (line) pressure of 15 pounds per square inch, to a stainless steel casting head whose dimensions were 6 inches by ¼ inch. The casting head was placed about ½ inch above the backing material, an 8 inch wide roll of kraft paper. The speed of the conveying system, i.e., the rate at which the paper was being pulled through the system was 8 feet per minute. A Van de Graaff accelerator was operated at 1,500 microamps, 1.5 MeV, and a scan width of 15 inches.

Good control over the dimensions of the thickened solution was obtained. The width of the initial cast (6 inches) did not increase measurably due to flow of the thickened solution toward the (side) edges of the paper backing. Since the casting head was about 8 feet from the accelerator (and the cast solution passed beneath the accelerator window at a vertical distance of 2 feet), the control of the dimensions of the cast solution lasted a little over one minute.

The cast solution was exposed to a dose of 1 Mrad at a variable dose rate of up to 0.13 Mrads/sec. A tap water capacity of 290 and a gel strength of 0.9 p.s.i. were measured for the product hydrogel.

EXAMPLE 8

Another 34 gallon batch of a 19 weight percent potassium acrylate 34 weight percent acrylamide solution was prepared as described in Example 7. Enough poly (acrylamide) from the same source as in Example 7 was added to make the concentration 3 percent by weight. However, the shearing forces to which the thickened solution was subjected to resulted in a viscosity of 22,000 centipoise. This thickened solution was irradiated under similar conditions as in Example 7 except that the conveyor speed was 7 feet/minute. Again good control over the thickened solution was observed. A tap water capacity of 255 and a gel strength of 1.5 p.s.i. were measured for the product hydrogel.

EXAMPLE 9

EFFECTIVENESS OF GELS AS BATTERY SEPARATORS

A stock solution of 41 percent by weight potassium acrylate was made in a manner similar to that used in Example 1 except that potassium hydroxide was used as the base. A portion of this solution, 1.66 gallons or 15.5 pounds, was mixed with 11.25 pounds of acrylamide powder and 2 gallons or 16.7 pounds of deionized water. This solution may be described as 13.6 percent potassium acrylate and 24.1 percent acrylamide by weight. To this monomer solution was added 1.3 pounds of high molecular weight poly (ethylene oxide), coagulent grade (commercially available from Union Carbide Corporation, 270 Park Avenue, New York, N.Y. 10017). In addition, 2 pounds of mercurous chloride and 2 pounds of para diphenyl polyethylene glycol (PPPG) were added to the solution. Mercurous chloride and PPPG are corrosion inhibitors for a zinc anode. The resulting solution had a viscosity of $10^5$ centipoise and was cast in a manner similar to Example 7 onto an absorbent material, an uncoated white paper backing containing no binders or other additives (S 1701 commercially available from Appleton Paper Co., Wis.). The thickness of the solution was controlled so that an approximately 0.01 inch coating of solution was applied to the paper backing.

The composite (paper and solution) was then conveyed at a speed of 3 feet per minute through an irradiation field. A 1.5 MeV Van de Graaff accelerator was operated at 1,500 microamps and a scan width of 15 inches. The composite was conveyed at a vertical distance of 2 feet below the accelerator window. The dose was 2.7 Megarads and the variable dose rate was up to 0.13 Megarads per second. A smooth pinhole-free coating was obtained on the paper. The coated paper was evaluated as a battery separator by inserting it into a "D"-size standard alkaline battery by standard procedures. The battery was tested for leakage (did not short out rapidly); service (length of time it functioned); and mix penetration. The results were that the coated paper functioned as well as commercially available battery separators.

EXAMPLE 10

VISCOSITY OF THICKENED MONOMER SOLUTIONS AS A FUNCTION OF CONCENTRATION OF POLYACRYLAMIDE OR HYDROXYETHYLCELLULOSE

Six liters (6600 grams) of a stock solution consisting of 19 weight percent potassium acrylate and 35 weight percent acrylamide (hereinafter referred to as "the 19-35 stock solution") were made by the procedures outlined in Example 7. To six separate 880 gram portions of this solution, high molecular weight poly (acrylamide) (American Cyanamid P-250) was added in amounts sufficient to provide six solutions whose poly (acrylamide) concentrations were 1, 2, 3, 4, 5, and 6 weight percent, respectively.

Similarly, 3 additional liters of the 19-35 stock solution were prepared. To four separate 500 gram portions of this solution, high molecular weight hydroxyethyl cellulose (CELLOSIZE QP, 100 M commercially available from Union Carbide Corporation, 270 Park Avenue, New York, N.Y. 10017) was added in amounts sufficient to provide four solutions whose hydroxyethylcellulose (hereinafter referred to as "HEC") concentrations were 1, 2, 3 and 4 weight percent, respectively.

Viscosity of the ten thickened solutions was measured with a Brookfield viscometer. The results are summarized in Table IX below. It is noted that HEC thickened these monomer solutions considerably better than it thickens water. This additional viscosity building characteristic of HEC was unexpected. Also, smaller concentrations of HEC (compared with poly (acrylamide) provided thickened solutions with larger viscosities.

Table IX summarizes the results of the viscosity tests hereinbelow:

TABLE IX

VISCOSITY OF MONOMER SOLUTIONS*
THICKENED WITH POLY (ACRYLAMIDE)

| Concentration | Viscosity (centipoise) | |
|---|---|---|
| (weight percent) | Poly (acrylamide) | HEC |
| 1 | 175 | 60,600 |
| 2 | 1,800 | 824,000 |
| 3 | 30,000 | 2,550,000 |
| 4 | 77,000 | 5,720,000 |
| 5 | 356,000 | N.D. |
| 6 | 610,000 | N.D. |

N.D. - not determined
*19-35 stock solution 28.9 grams of poly (ethylene oxide) (POLYOX, coagulent grade, molecular weight of $5 \times 10^6$ commercially available from Union Carbide Corporation, 270 Park Avenue, New York, N.Y. 10017) was added to 550 grams of the 19-35 stock solution. Viscosity of the thickened solution was measured to be at least 100,000. It should be noted that poly (ethylene oxide) is sensitive to high salt concentrations. Hence, it would not be a good thickener for monomer solutions containing very high potassium acrylate concentrations e.g. it did not thicken a 41 percent potassium acrylate solution.

Ground up "fine particles" of a hydrogel made according to the method of this invention from a 19-35 stock solution containing 3 weight percent poly (acrylamide) (American Cyanamid P-250) the fine particles sized smaller than 60 mesh were added to a separate 19-35 stock solution in concentrations of 2, 3, 4, 5, 6 and 7 weight percent. Viscosities of 100 (at 2 weight percent) to one million (at 7 weight percent) were measured illustrating the effectiveness of the "fine particles" as a thickening agent.

EXAMPLE 11

2,000 pounds of a 50 weight percent acrylamide solution, 451 pounds of acrylic acid and 768 pounds of 50 weight percent potassium hydroxide solution were admixed. This solution may be characterized as 23 weight percent potassium acrylate and 32 weight percent acrylamide. 99.5 pounds of poly (acrylamide) (American Cyanamid P-250) was added to this solution. Then, the solution was agitated for several days in a 400 gallon stainless steel tank at 28 RPM. The shearing action resulted in the viscosity of the solution being 8,640 centipoise. The solution was cast onto a conveyor belt as described in Example 7 without difficulties. It was also cast onto an open mesh scrim onto a steel belt and onto a steel drum. Adequate control of the thickened solution was obtained in each case.

EXAMPLE 12

An aqueous solution of acrylamide and potassium acrylate was made according to procedures used in Example 10. In this case, the concentrations were 22 weight percent potassium acrylate and 40 weight percent acrylamide. Two 1000 cc portions of this solution were set aside. To one 1000 cc portion, 50 grams of poly (acrylamide) (American Cyanamide P-250) was added to provide a concentration of 5 percent by weight. Nothing was added to the other portion.

Both portions were irradiated with a 1.5 MeV Van de Graaff accelerator at 40 microamps with an 8 inch scan width. 50 cc of the portions were placed in Petri dishes on a conveyor belt which was positioned at a close distance from the accelerator window (~2 inches). The conveyor speed was 3 feet per minute. These conditions combine to deliver a dose of 0.25 Mrad/pass at a dose rate of 0.3 Mrad/second. At a dose of 0.5 Mrad, the portion containing no thickener was polymerized but when it was placed into water, the hydrogel had no strength at all and appeared to be slimy rather than swollen particles. On the other hand, the solution portion containing the thickening agent formed a soft hydrogel with a tap water capacity of 563.

While the hydrogel made from thickened solution was probably too soft for many end applications, the difference between the hydrogels was striking and was indicative of the general trend noted with solutions containing thickening agents. A further indication that more efficient polymerization is occurring comes from measurements of the residual monomers in these two portions.

The hydrogel made from the thickened solution had a residual monomer content of approximately 1.08 weight percent, while the hydrogel made from the unthickened solution had a residual monomer content of 1.52 weight percent (measured as in Example 2).

Additional doses were given to additional sample solutions prepared as described in this example. The irradiation conditions were identical except that the number of passes through the irradiation field was varied in order to achieve doses of 0.75 Mrad and 1 Mrad. The results are summarized in Table X hereinbelow:

TABLE X
EFFECT OF THICKENER
(5 PERCENT POLY (ACRYLAMIDE))
ON PROPERTIES OF GELS

| Dose (Mrad) | Capacity in Tap Water | Gel Strength | Residual Monomer (%) |
|---|---|---|---|
| Unthickened Solution* | | | |
| 0.5 | N.D. | Weak, runny, pituitous | 1.52 |
| 0.75 | N.D. | " | .88 |
| 1 | 647 | Soft | .72 |
| Thickened Solution* | | | |
| 0.5 | 563 | Soft | 1.08 |
| 0.75 | 324 | Semi-Firm | .52 |
| 1 | 237 | Firm | .40 |

*Solution was 22 percent potassium acrylate and 40 percent acrylamide.

EXAMPLE 13

3 liters of a 19-35 stock solution were prepared by the procedures used in Example 10. To a portion of this solution was added a sufficient amount of poly (acrylamide), (American Cyanamid P-250), to make its concentration 3 weight percent. These solution samples were irradiated about 2 inches from the window using the 1.0 MeV Van de Graaff accelerator at 160 microamps and a scan width of 8 inches at 3 feet/minute. These conditions combine to give a dose of 1 Mrad/pass at a dose rate of 1.2 Mrad/second. Table XI illustrates the trend, similar to that shown in Example 12, that the presence of the thickening agent leads to firmer hydrogels at equivalent doses. The trend may be interpreted as the thickening agent leading to less dose required for the hydrogel to attain equivalent properties. Residual monomer content was measured as described in Example 2.

TABLE XI
EFFECT OF THICKENER
(3 PERCENT POLY (ACRYLAMIDE))
ON GEL PROPERTIES

| Dose (Mrad) | Capacity in Tap Water | Gel Strength | Residual Monomer (%) |
|---|---|---|---|
| No Thickener | | | |
| 1 | N.D. | Slimy Gel | 2.28 |
| 2 | 306 | Soft | .56 |
| 3 | 175 | Firm | .32 |
| 4 | 129 | Firm | .22 |
| 5 | 106 | Very Firm | .26 |
| Thickener Present | | | |
| 1 | 426 | Very Soft | 2.48 |
| 2 | 233 | Soft | .48 |
| 3 | 124 | Firm | .30 |
| 4 | 78 | Very Firm | .19 |
| 5 | 60 | Very Firm | .22 |

EXAMPLE 14

By the procedures used in Example 10, a 19-35 stock solution was prepared. To this solution sufficient HEC (CELLOSIZE QP 52,000) was added to make the final concentration 0.75 percent by weight. 30 cc of this thickened solution were irradiated at one time at 1200 microamps using a 1.5 MeV Van de Graaff accelerator and a scan width of 15 inches, in Petri dishes on a conveyor positioned 2 feet below the accelerator window. A variable dose rate up to 0.1 Mrad/sec and total dose of approximately 1 Mrad was delivered to each target solution.

Conveyor speeds run were 7, 8, 9, 10, 12, 15, 20 and 30 feet per second. At conveyor speeds of 7 and 8 feet per second, gel strengths of product hydrogels were found to be 1.5 p.s.i.; 0.9 p.s.i. at conveyor speeds of 9, 10 and 12 feet/sec; 1.0 p.s.i. at conveyor speeds of 20 and 30 feet per second. Salt water capacities (in 0.3 N NaCl) for the product hydrogels at the conveyor speeds of 7 to 30 feet per second were found to be 38, 39, 59, 61, 67, 43, 33 and 25, respectively.

Firm gels were obtained at all conditions tested, for conveyor speeds from 7 feet/minute to 30 feet/minute. Normally with no thickener or with poly (acrylamide) thickener, no gels are formed, or at best, very soft, soupy gels are made at line speeds over 12 feet/minute. At conveyor speeds of 9, 10, and 12 feet/minute, materials having gel strengths or 0.9 pounds/square inch or higher and capacities in salt water solution of 33 or higher. These are excellent properties. "Normal" solutions need considerably larger doses, 6 or 7 feet/minute, to produce acceptable material having adequate gel strengths and capacities.

EXAMPLE 15

A 19.7 weight sodium acrylate and 17.9 weight percent acrylamide solution was made according to the procedures used in Example 3. A 50 weight percent talc—50 weight percent monomer solution was then made by admixture of talc to this solution. The mixture was irradiated at 1.2 Mrad/sec with a 1.0 MeV Van de Graaff accelerator to form a hydrogel. When dried, the composite contained 26.5 weight percent of polymeric hydrogel with the remainder being talc. At an irradiation dose of 2 Mrad, the composite absorbed 20.3 times its weight in saline solution (0.3 N NaCl).

Also 15 cc of a 32.2 weight percent sodium acrylate and 8.7 weight percent acrylamide (made according to the procedure of Example 3) were added respectively, to 50 grams of vermculite, perlite, and polyurethane foam and subjected to 1, 2, 3 and 4 Mrad dose with a 1.0 MeV Van deGraaff accelerator. The dose rate was 1.2 Mrad/sec. Absorbent products were produced in all cases. 15 cc of the 32.2 sodium weight percent acrylate and 8.7 weight percent acrylamide solution of this example was admixed with 20 grams of perlite and subjected to 1 Mrads under the conditions outlined herein this example. A tap water capacity for the composite produced was measured to be 173.

In describing the present invention, certain embodiments have been used for illustrative purposes. However, other embodiments and modifications within the spirit and scope of the invention will readily occur to those skilled in the art in light of this disclosure. The invention is accordingly not to be limited to the specific embodiments illustrated.

What is claimed is:

1. A method of preparing an insoluble polyelectrolyte hydrogel capable of absorbing more than about 20 times its weight in aqueous solution which comprises:

forming a predetermined mass comprised of a mixture of an acrylate salt and acrylamide in a ratio of acrylate salt to acrylamide between about 0.3 to 1 and about 20 to 1, the predetermined mass having a pH in solution between about 6 and about 12; and exposing the predetermined mass to a dose of from about 0.2 to about 10 Megarads of ionizing radiation at a dose rate between about 0.001 Megarads per second and about 10 Megarads per second for a time period sufficient to form said hydrogel which is substantially free of unreacted monomer.

2. A method as defined in claim 1 wherein said predetermined mass is an aqueous solution.

3. A method as defined in claim 2 wherein said aqueous solution is formed by contacting acrylamide with acrylic acid, water and a base.

4. A method as defined in claim 1 wherein said predetermined mass further includes a thickening agent.

5. A method as defined in claim 4 wherein said thickening agent comprises poly (acrylamide).

6. A method as defined in claim 5 wherein said polyacrylamide is high molecular weight polycarylamide and is present in a concentration between about 1 and about 6 percent by weight of said predetermined mass.

7. A method as defined in claim 4 wherein said thickening agent comprises poly (ethylene oxide).

8. A method as defined in claim 7 wherein said poly (ethylene oxide) is high molecular weight poly (ethylene oxide) and is present in a concentration between about 1 and about 6 percent by weight of said predetermined mass.

9. A method as defined in claim 4 wherein said thickening agent comprises hydroethylenecellulose (HEC).

10. A method as defined in claim 9 wherein said HEC is high molecular weight HEC and is present in a concentration between about 0.5 and about 4 percent by weight of said predetermined mass.

11. A method as defined in claim 4 wherein said thickening agent comprises insoluble polyelectrolyte hydrogel particles made according to claim 1 and sized finer than 60 mesh, said hydrogel particles being present in a concentration between about 2 and about 7 percent by weight of said predetermined mass.

12. A method as defined in claim 1 wherein said predetermined mass further includes a processing additive comprising an absorbent or filler material.

13. A method as defined in claim 12 wherein said processing additive comprises a material selected from the group consisting of cellulose, silica, bentonite, wood flour, paper, perlite, vermiculite, hydrophilic polyurethane foam and combinations thereof.

14. A method as defined in claim 1 wherein said predetermined mass further includes a water soluble polymer selected from the group consisting of starch, modified starch, Guar gum, Xanthan gum, poly (vinyl pyrrollidone), poly (ethylene imne), methyl cellulose, hydroxypropyl cellulose, sodium carboxymethyl cellulose, poly (acrylic acid), poly (methacrylic acid), poly (methacrylamide), polyethylene sulfonate, polystyrene sulfonate and combinations thereof.

15. A method as defined in claim 1 wherein said ionizing radiation has an energy level in the range of about 0.10 MeV to about 20 MeV.

16. A method as defined in claim 3 wherein said base is an alkali metal hydroxide.

17. A method as defined in claim 3 wherein said base is ammonium hydroxide.

18. A method as defined in claim 1 wherein said acrylate salt is selected from the group consisting of acrylate salts of an alkali metal, ammonoum, calcium, magnesium, tin, lead, strontium, nickel, zinc, barium, cobalt, cadmium and mixtures thereof.

19. A method as defined in claim 1 wherein said hydrogel has a gel strength greater than about 0.3 p.s.i.

20. A method as defined in claim 1 wherein in said predetermined mass, said acrylate salt is present in a concentration between about 20 and about 40 weight percent and said acrylamide is present in a concentration of up to about 25 weight percent.

21. A method as defined in claim 20 wherein said acrylate salt is present in a concentration of about 30 weight percent.

22. A method as defined in claim 20 wherein said acrylamide is present in a concentration between about 1 and about 10 weight percent.

23. A method as defined in claim 1 wherein in said predetermined mass, said acrylate salt is present is a concentration up to about 20 weight percent and said acrylamide is present in a concentration between about 20 and about 50 weight percent.

24. The hydrogel of claim 1.

25. An absorbent product prepared by drying the hydrogel of claim 24 to remove at least some of the water.

26. A disposable absorbent article containing at least one of the absorbent products of claim 25.

27. An absorbent article containing at least one of the absorbent products of claim 25.

28. A method of preparing an insoluble polyelectrolyte hydrogel capable of absorbing more than about 20 times its weight in aqueous solution which comprises:

forming a predetermined mass comprised of a mixture of an acrylate salt and acrylamide in a ratio of acrylate salt to acrylamide between about 0.3 to 1 and about 20 to 1, the predetermined mass having a pH between about 6 and about 12; and exposing said predetermined mass to a dose of from about 0.2 to about 10 Megarads of ionizing radiation at a dose rate varying in intensity between a first level and a second level for a time period sufficient to form said hydrogel which is substantially free of unreacted monomer.

29. A method as defined in claim 28 wherein said ionizing radiation has an energy level in the range of about 0.10 MeV to about 20 MeV.

30. A method as defined in claim 28 wherein said predetermined mass comprises an aqueous solution formed by contacting acrylamide with acrylic acid, water and a base.

31. A method as defined in claim 30 wherein said base is an alkali metal hydroxide.

32. A method as defined in claim 30 wherein said base is ammonium hydroxide.

33. A method as defined in claim 28 wherein said acrylate salt is selected from the group consisting of acrylate salts of alkali metal, ammonium, calcium, magnesium, tin, lead, strontium, nickel, zinc, barium, cobalt, cadmium and mixtures thereof.

34. A method as defined in claim 28 wherein said hydrogel has a gel strength greater than about 0.3 p.s.i.

35. A method as defined in claim 28 wherein in said predetermined mass, said acrylate salt is present in s concentration between about 20 and about 40 weight percent and said acrylamides is present in a concentration of up to about 25 weight percent.

36. A method as defined in claim 35 wherein said acrylate salt is present in a concentration of about 30 weight percent.

37. A method as defined in claim 35 wherein said acrylamide is present in a concentration between about 1 and about 10 weight percent.

38. A method as defined in claim 28 wherein in said solution, said acrylate salt is present in a concentration up to about 20 weight percent and said acrylamide is present is a concentration between about 20 and about 50 weight percent.

39. A method as defined in claim 28 wherein said first level is about 0.001 Megarads per second and said second level is about 0.5 Megarads per second.

40. The hydrogel of claim 28.

41. An absorbent product prepared by drying the hydrogel of claim 40 to remove at least some of the water.

42. A disposable absorbent article containing at least one of the absorbent products of claim 41.

43. An absorbent article containing at least one of the absorbent products of claim 41.

44. A method as defined in claim 28 wherein said predetermined mass further includes a thickening agent.

45. A method as defined in claim 44 wherein said thickening agent comprises poly (acrylamide).

46. A method as defined in claim 45 wherein said polyacrylamide is high molecular weight polyacrylamide and is present in a concentration between about 1 and about 6 percent by weight of said predetermined mass.

47. A method as defined in claim 44 wherein said thickening agent comprises poly (ethylene oxide).

48. A method as defined in claim 47 wherein said poly (ethylene oxide) is high molecular weight poly (ethylene oxide) and is present in a concentration between about 1 and about 6 percent by weight of said predetermined mass.

49. A method as defined in claim 44 wherein said thickening agent comprises hydrooxyethylcellulose (HEC).

50. A method as defined in claim 49 wherein said HEC is high molecular weight HEC and is present in a concentration between about 0.5 and about 4 percent by weight of said predetermined mass.

51. A method as defined in claim 44 wherein said thickening agent comprises insoluble polyelectrolyte hydrogel particles made according to claim 1 and sized finer than 60 mesh, said hydrogel particles being present in a concentration between about 2 and about 7 percent by weight of said predetermined mass.

52. A method as defined in claim 28 wherein said predetermined mass further includes a processing additive comprising an absorbent or filler material.

53. A method as defined in claim 52 wherein said processing additive comprises a material selected from the group consisting of cellulose, silica, bentonite, wood flour, paper, perlite, vermiculite, hydrophilic polyurethane foam and combinations thereof.

54. A method as defined in claim 28 wherein said predetermined mass further includes a water soluble polymer selected from the group consisting of starch, modified starch, Guar gum, Xanthan gum, poly (vinyl pyrrollidone), poly (ethylene imine), methyl cellulose, hydroxypropyl cellulose, sodium carboxymethyl cellulose, poly (acrylic acid), poly (methacrylic acid), poly (methacrylamide), polyethylene sulfonate, polystyrene sulfonate and combinations thereof.

* * * * *

UNITED STATES PATENT AND TRADEMARK OFFICE
CERTIFICATE OF CORRECTION

PATENT NO. : 4,192,727  
DATED : March 11, 1980  
INVENTOR(S) : James A. Ward

It is certified that error appears in the above—identified patent and that said Letters Patent is hereby corrected as shown below:

Column 8, line 24,

"entrace" should read -- entrance --.

Column 8, lines 27 and 28,

"Van de Graff" should read -- Van de Graaff --.

Column 9, line 15,

"acqueous" should read -- aqueous --.

Column 9, line 40,

"pyrrollidone" should read -- pyrrolidone --.

Column 12, lines 44 and 45,

After the word "predetermined" insert the word "target".

UNITED STATES PATENT AND TRADEMARK OFFICE
CERTIFICATE OF CORRECTION

PATENT NO. : 4,192,727
DATED : March 11, 1980
INVENTOR(S) : James A. Ward

It is certified that error appears in the above-identified patent and that said Letters Patent are hereby corrected as shown below:

Column 15, line 48,

"get" should read -- gel --.

Column 16, see heading in Table III, line 20,

"3.23%" should read -- 32.3% --.

Column 19, see subheading "Gel Strength (P.S.I.)"

"Conveyor Speed 4" should read -- Conveyor Speed = 4 --.

Column 23, line 1,

Sentence beginning with the word "The" should not be a new paragraph.

UNITED STATES PATENT AND TRADEMARK OFFICE
CERTIFICATE OF CORRECTION

PATENT NO. : 4,192,727
DATED : March 11, 1980
INVENTOR(S) : James A. Ward

It is certified that error appears in the above—identified patent and that said Letters Patent is hereby corrected as shown below:

Column 25, line 25,

"polycarylamide" should read -- polyacrylamide --.

Column 25, lines 58 and 59,

"pyrrollidone" should read -- pyrrolidone --.

Column 25, line 59,

"(ethylene imne)" should read -- (ethylene imine) --.

Column 26, line 5,

"ammonoum" should read -- ammonium --.

Column 26, line 67,

"s" should read -- a --.

Column 27, line 12,

"is" should read -- in --.

UNITED STATES PATENT AND TRADEMARK OFFICE
CERTIFICATE OF CORRECTION

PATENT NO. : 4,192,727           Page 4 of 4

DATED : March 11, 1980

INVENTOR(S) : James A. Ward

It is certified that error appears in the above—identified patent and that said Letters Patent is hereby corrected as shown below:

Column 28, line 31,

"pyrrollidone" should read -- pyrrolidone --.

Signed and Sealed this

Seventh Day of October 1980

[SEAL]

Attest:

SIDNEY A. DIAMOND

Attesting Officer      Commissioner of Patents and Trademarks